United States Patent
Doll et al.

(10) Patent No.: US 7,947,048 B2
(45) Date of Patent: May 24, 2011

(54) SCREWDRIVER FOR HANDLING A SCREW IN THE BODY OF A PERSON OR AN ANIMAL

(75) Inventors: Frank Doll, Talheim (DE); Christian Walter, Emmingen-Liptingen (DE)

(73) Assignee: Karl Storz GmbH & Co. KG (DE)

( * ) Notice: Subject to any disclaimer, the term of this patent is extended or adjusted under 35 U.S.C. 154(b) by 868 days.

(21) Appl. No.: 11/862,336

(22) Filed: Sep. 27, 2007

(65) Prior Publication Data
US 2008/0082106 A1    Apr. 3, 2008

(30) Foreign Application Priority Data
Sep. 28, 2006    (DE) .................. 10 2006 047 674

(51) Int. Cl.
*A61B 17/58* (2006.01)
(52) U.S. Cl. ........................ 606/104; 606/916
(58) Field of Classification Search ............... 606/86 A, 606/86 B, 99, 101, 104, 138, 914–916
See application file for complete search history.

(56) References Cited

U.S. PATENT DOCUMENTS

| | | | |
|---|---|---|---|
| 2,312,869 A | | 3/1943 | Boyer |
| 2,796,009 A | * | 6/1957 | Doyle et al. |
| 6,189,422 B1 | | 2/2001 | Stihl |
| 6,679,248 B2 | * | 1/2004 | Stadelhofer .............. 128/200.14 |
| 2003/0199983 A1 | * | 10/2003 | Michelson ................ 623/17.16 |
| 2006/0111712 A1 | * | 5/2006 | Jackson ........................ 606/61 |

FOREIGN PATENT DOCUMENTS

| | | | |
|---|---|---|---|
| CH | 368761 A | * | 4/1963 |
| DE | 3804749 | | 3/1989 |
| DE | 19832303 | | 1/2000 |

OTHER PUBLICATIONS

European Search Report, EP07019070, Oct. 1, 2008, 5 pages.

\* cited by examiner

*Primary Examiner* — Eduardo C Robert
*Assistant Examiner* — Sameh Boles
(74) *Attorney, Agent, or Firm* — St. Onge Steward Johnston & Reens LLC

(57) ABSTRACT

A screwdriver serves for handling a screw in the body of a person or an animal. The screwdriver has a handle, and a stem permanently connected to said handle. An outer tube surrounds the stem. A locking mechanism has a locking element engaging into a locking point in at least three different axial displacement positions of said outer tube. The locking element is prevented from moving further in an axial direction at a locking position by a barrier, which barrier can be overcome only by rotating said outer tube and said stem relative to one another about a longitudinal axis.

16 Claims, 4 Drawing Sheets

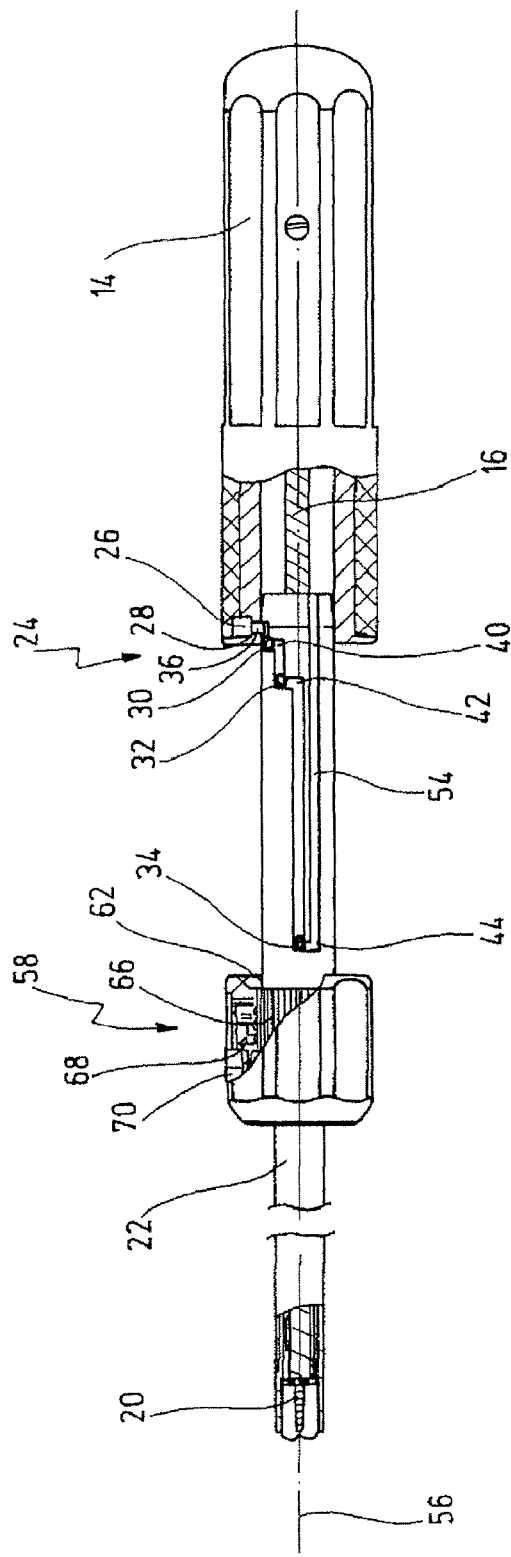
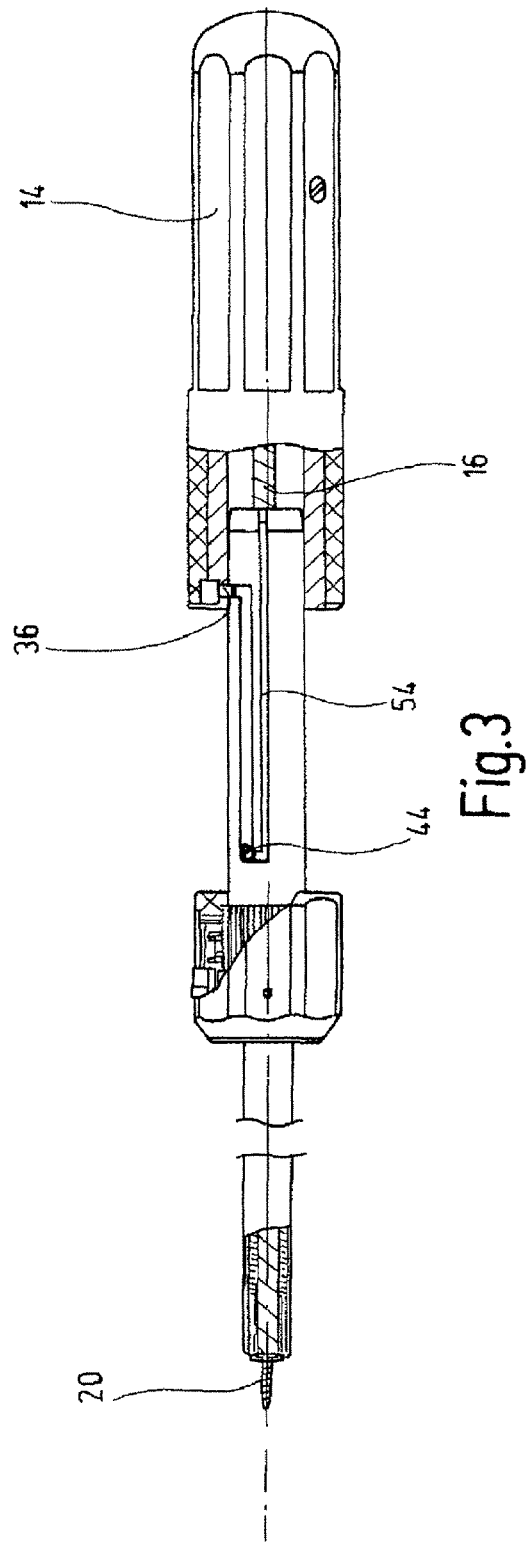

SCREWDRIVER FOR HANDLING A SCREW IN THE BODY OF A PERSON OR AN ANIMAL

BACKGROUND OF THE INVENTION

The invention relates to a screwdriver for handling a screw in the body of a person or an animal, comprising a handle having a stem which is permanently connected to the handle and to whose distal end a screw can be fitted.

A screw driver of this kind is known from U.S. Pat. No. 6,189,422 B1.

For holding the screw at the screwdriver during inserting it into the body, the known screwdriver has a first inner tubular shaft surrounding the stem. The inner shaft has a clamping gripper at its distal end for clamping and holding the screw. A second outer tubular shaft surrounds the inner shaft and is displaceable axially relatively to the inner shaft and relatively to the stem.

In a first position, the outer shaft is displaced in an axial direction to such an extent that the clamping gripper of the inner shaft is pushed radially inwardly thereby clamping the screw attached to the stem. The assembly of the two displaceable shafts is locked in that position via a locking element which is a spring based ball entering into a circumferential groove.

In that position, the screwdriver can be inserted into the body for example via a trokar.

In a second position, the outer tube is displaced proximally to an extent, that the screw comes free from the clamping gripper. The screw is now free for turning it with the stem. In that second position, the assembly of the two shafts is again locked via the locking element.

In a third position, both shafts are moved proximally to an extent that the distal end of the stem protrudes both shafts. The screw can now be released from the stem.

In the third position, the assembly of outer and inner shaft is again locked via the locking element.

A control allows the movement of the two shafts via an outer slider. The slider can be moved only in axial directions between the three axial different displacement positions.

The spring based ball locks the slider in the three positions. When exerting a force on the slider, the ball comes out of the locking position, slides along an axial direction into the axial next locking position. A disadvantage is that if too much force is acted on the slider, it slides from the first position to the third position giving the screw free. This means, the second position is overrun if too much force is acted on the slider.

If that occurs, the screw may be lost in the body without having turned it in.

For assembling and disassembling the screw driver, the slider can be turned about the longitudinal axis giving the two shafts free for removal.

The connection between the slider and the two shafts occurs via two control elements mounted in the slider with laterally projecting pins at the proximal end of the two shafts.

When assembling the screw driver, the two shafts are inserted into the slider, and a turning movement of the slider locks the two shafts at the screw driver.

But, this turning movement of the slider occurs only when assembling or disassembling the screwdriver for cleaning it or for preparing it for a surgery.

During a surgery, the surgeon only performs the axial sliding movements of the slider with the risk of overrunning the intermediate position.

It is therefore an object of the present invention to develop a screwdriver in that the outer tube can be moved into the different displacement positions with respect to the stem and locked in these displacement positions without one or more locking points having to be jumped over.

SUMMARY OF THE INVENTION

According to the invention, this object is achieved by a screwdriver comprising a handle, a stem permanently connected to said handle, said stem having a distal end to which a screw can be fitted, an outer tube surrounding said stem, and a locking mechanism for locking said outer tube in at least three different axial displacement positions relative to said stem, said locking mechanism having a locking element engaging into a locking point in each of said three different displaced displacement positions of said outer tube, wherein said locking element is prevented from moving further in an axial direction at each locking point by a barrier, said barrier can be overcome only by rotating said outer tube and said stem relative to one another about a longitudinal axis.

These measures have the considerable advantage that the possibility of one or more locking points being run over is completely ruled out by the formation of the barrier for preventing further axial forward movement.

In order to overcome the mechanical obstruction, the operator has to rotate the stem and the outer tube relative to one another about a longitudinal axis. This ensures that during an axial displacement of the outer tube no uncontrolled running over of one or more locking points occurs so that the insertion and the screwing in of the screw in the body of a person or animal can be carried out in an overall atraumatic way. This also has the advantage that the handling of the screwdriver is easy for the operator and the activation can be carried out without particular attention. The operator does not need to get the feeling in which of the three axially different positions he is. He can always move up to the mechanical obstruction.

In a further embodiment of the invention, the locking element runs in a guide whose path deviates from the longitudinal axis by an angle α from one locking point to the next locking point.

The guide of the locking element has the advantage that the path of the locking element which moves from one locking point to the next locking point is determined by the guide, i.e. the advantage that the locking element can be moved only along the path.

The fact that the path, i.e. a permanently predefined distance which the locking element travels along from one locking point to the next locking point, deviates from the longitudinal axis by the angle α ensures that the locking element is not moved from one locking point to the next locking point by an axial movement but rather by the movement which deviates from the axial movement. The barrier is an end of the path stopping the locking element against further axial movement.

In a further embodiment of the invention, the angle α is preferably 30° to 90°, in particular approximately 90°.

This measure has the advantage that the angle α in the abovementioned angle range provides sufficient mechanical obstruction preventing further forward movement in the axial direction.

In a further embodiment of the invention, the path is embodied as a groove in the outer tube.

This measure has the advantage that the groove constitutes a mechanically simple guide for the locking element, which means it is also easy to manufacture.

In a further embodiment of the invention, the locking element is embodied as a pin.

This measure has the advantage of providing a structurally simple locking element which brings about a sufficiently secure latched connection at the locking points.

In a further embodiment of the invention, the pin is spring-loaded.

The spring loading provides defined friction between the locking element and path, which friction gives the operator feedback about his handling.

Furthermore, the pin is pressed into the locking points by means of the spring loading so that a sufficient latched connection can be brought about.

In a further embodiment of the invention, the locking element projects from an inner side of the handle.

This measure has the advantage that these components do not disrupt the gripping and handling of the handle.

In a further embodiment of the invention, the locking points are arranged at a proximal end of the outer tube.

This measure has the advantage that the aforesaid locking mechanism is arranged at the proximal section of the screwdriver which does not penetrate the body and is thus protected against contamination from body fluids.

In a further embodiment of the invention, a proximal end section of the outer tube can be rotated about its longitudinal axis.

This measure has the advantage that in the latched state the handle together with the stem and screw as well as the section of the outer tube which is latched to the handle can be rotated.

In a further embodiment of the invention, the outer tube is connected to the handle in a removable fashion.

This measure has the advantage that the parts of the screwdriver can be cleaned separately because it can be disassembled. In this way the screwdriver according to the invention meets the stringent requirements which are generally made of such medical instruments in terms of their disinfection and cleaning.

In a further embodiment of the invention, the proximal end section of the outer tube is connected to a coupling which runs freely to the right or left for the outer tube to rotate.

This measure has the advantage that the coupling provides and releases a non-positively locking connection between the handle and outer tube in one rotational direction depending on whether a screw is to be screwed in or unscrewed, with the result that a screw can be screwed in or unscrewed by the handle which is gripped continuously.

In a further embodiment of the invention, the locking points are embodied as depressions in the path.

This measure has the advantage that the locking point can be embodied, like the groove, by means of a simple processing operation. The spring-loaded pins can latch into these locking points. The corresponding clicking noise indicates to the operator that he has reached a locking point.

In a further embodiment of the invention, four locking points are provided.

This measure has the advantage that the outer tube can be locked in foul different displacement positions with respect to the stem.

In a further embodiment of the invention, a groove which is open at its proximal end is formed from the proximal end of the outer tube to the first locking point.

This measure has the advantage that by means of the open groove the outer tube can be connected to the handle in a particularly easy manoeuvre. In the assembly process, the spring-loaded pin is pushed into the open end of the groove. The handle is then moved in the proximal direction until the pin which projects from the inner side of the handle engages in the first locking point.

In a further embodiment of the invention, a groove which is open at its proximal end is also formed from the last locking point to the proximal end of the outer tube.

This measure has the advantage that the groove allows the outer tube and the handle to be separated from one another by virtue of the fact that the pin is guided from the last locking point as far as its open end along the groove. This facilitates a disassembly of the screwdriver after a use.

In a further embodiment of the invention, the groove is embodied in a step-like manner.

This measure has the advantage that such an embodiment of the groove allows the guide to be exact and predetermined and causes it to give the operator a good feeling as to which displacement state the device is in. The corners of the steps provide the barrier.

Of course, the features which are mentioned above and are to be explained below can be used not only in the respectively stated combination but also in other combinations or alone without departing from the scope of the present invention.

BRIEF DESCRIPTION OF THE DRAWINGS

The invention is described and explained below in more detail with reference to a selected exemplary embodiment and in conjunction with the drawings, in which:

FIG. 2 shows a screwdriver in an overall view, partially in longitudinal section along a longitudinal axis, with a locking element engaging in a first locking point in which the screw is completely surrounded by the outer tube, FIG. 3 shows an illustration which is comparable to the illustration in FIG. 2, with the locking element engaging in a third locking point in which the screw is exposed.

DETAILED DESCRIPTION OF PREFERRED EMBODIMENTS

Figure 1:
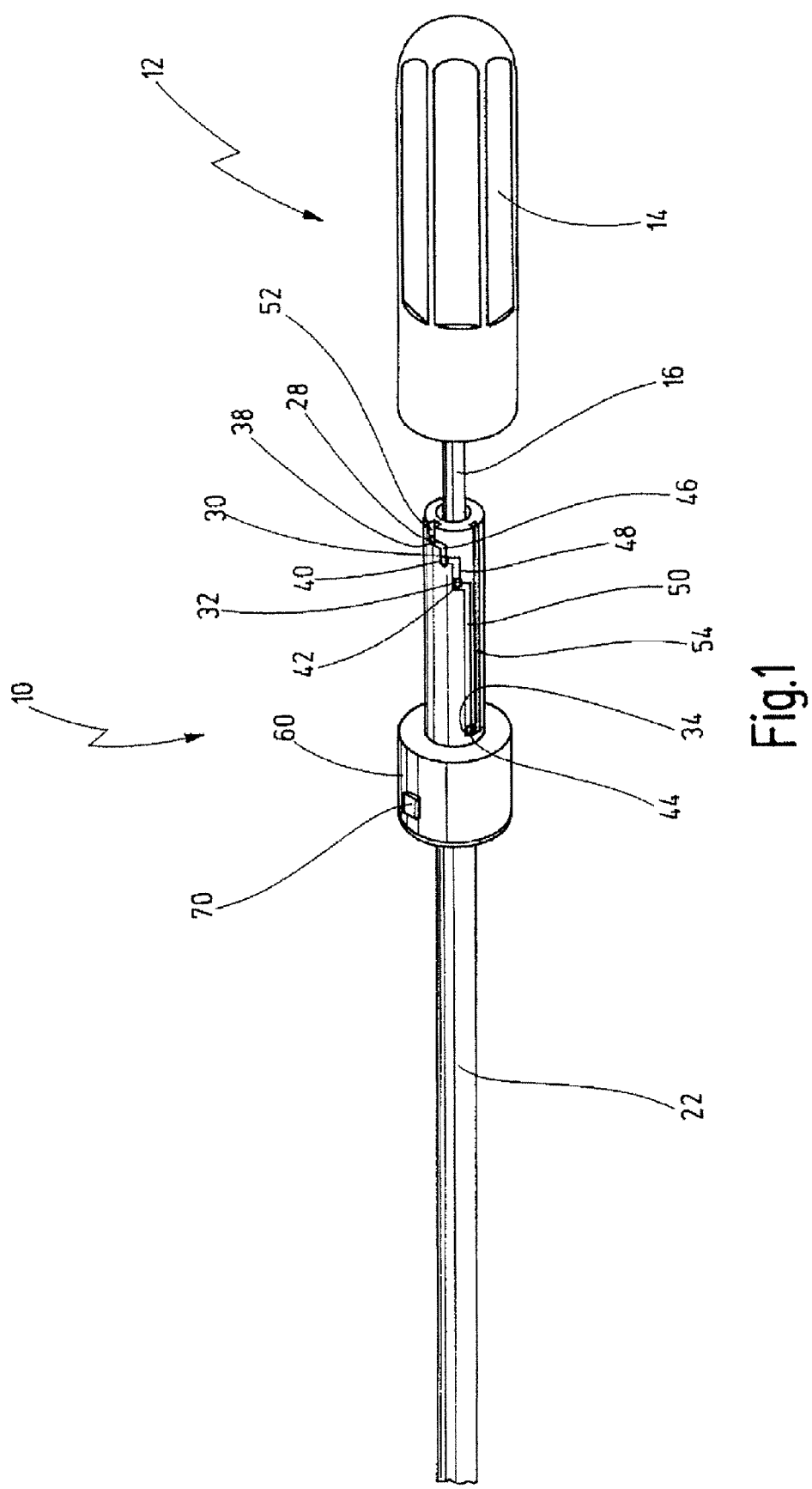
FIG. 1 shows a perspective side view of a screwdriver according to the invention in which the handle is inserted together with the stem into the outer tube but these components have not yet been connected to one another.

A screwdriver which is provided with the general reference number 10 is illustrated in FIG. 1. The screwdriver 10 serves to handle a screw in the body of a person or animal.

The screwdriver 10 has a handle 14 at a proximal end 12. A stem 16, which is only partially visible in FIG. 1, is permanently connected to the handle 14. The stem 16 is elongated and has a length of approximately 30 cm.

Figure 4:
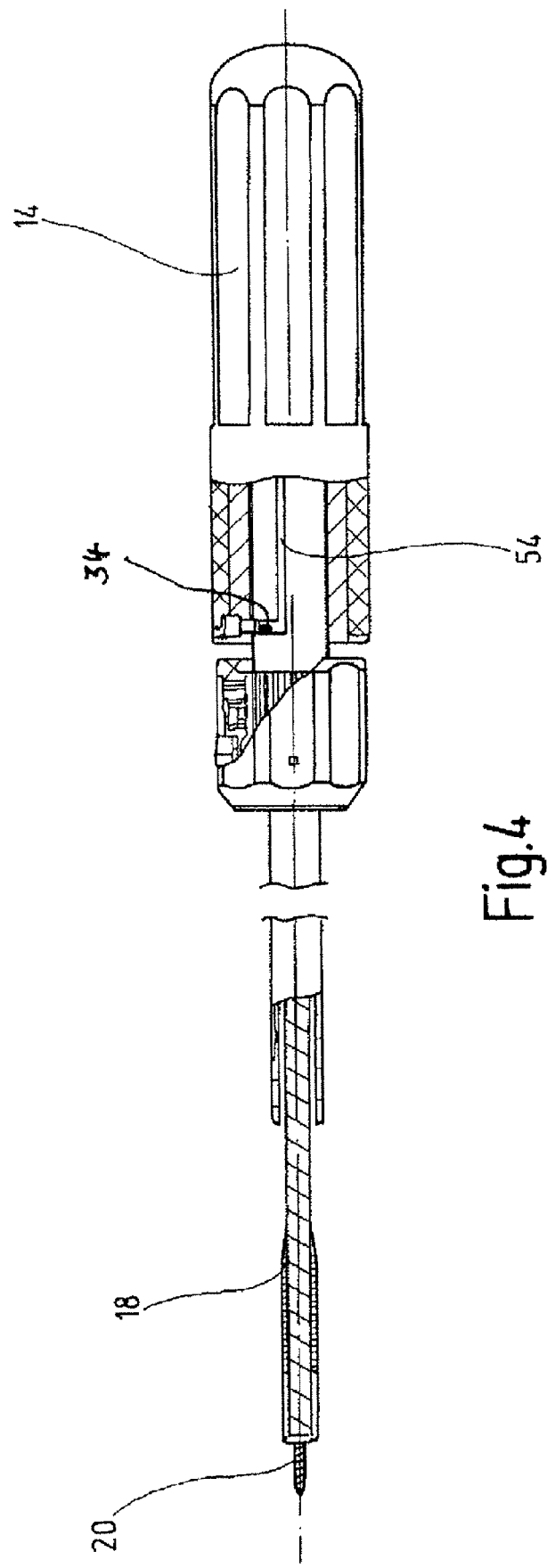
FIG. 4 shows an illustration which is comparable to the illustration in FIG. 2, with the locking element engaging in a fourth locking point in which the distal end region of the stem is pushed out of the outer tube.

The stem 16 has a head 18 at its distal end, as can be seen in particular in the illustration in FIG. 4. A screw 20 is fitted in a holder on the head 18.

The screwdriver 10 also has an outer tube 22. The outer tube 22 is connected to the handle 14 in a removable fashion. The two elements 14 and 22 are not yet connected to one another in the illustration in FIG. 1.

The screwdriver 10 also has a locking mechanism 24 (FIG. 2). The locking mechanism 24 is composed of two elements, specifically of a locking element 26 and a plurality of locking points 28, 30, 32, 34. The locking element 26, which can be seen in the illustration in FIG. 2, projects from an inner side of the handle 14.

The locking element 26 is embodied in this exemplary embodiment as a spring-loaded pin 36.

In this exemplary embodiment, the screwdriver 10 has four locking points 28, 30, 32, 34.

A guide 46 whose path 48, i.e. a permanently predefined distance which the locking element 26 travels along from one locking point to the next locking point, is embodied as a groove 50, is formed between the locking points 28, 30, 32, 34.

In this exemplary embodiment, the groove 50 is embodied in a step-like manner, specifically in such a way that in each case a right-angled step is arranged between two adjacent locking points 28, 30, 32, 34. The locking points 28, 30, 32, 34 are embodied as depressions 38, 40, 42, 44 in the path 48.

A groove 52 which is open at its proximal end is formed from the proximal end of the outer tube 22 to the first locking point 28. This groove 52 serves to allow the handle 14 to be fitted onto the outer tube 22 in the proximal direction during assembling.

A groove 54, which is also open at its proximal end, is formed from the fourth locking point 34 to the proximal end of the outer tube 22. In contrast, this groove 54 serves to allow the handle 14 and the outer tube 22 to be separated from one another during disassembling. The connection and the separation of the two elements 14, 22 will be described later in more detail.

The proximal end section of the outer tube 22 at which the locking points 28, 30, 32, 34 and the guide 46 are formed can be rotated about a longitudinal axis 56 (FIG. 2). A distal section of the outer tube 22 is rigid.

The rotatable section of the outer tube 22 is connected to a coupling 58 which runs freely to the right or left. The coupling 58 is arranged in a housing 60 which is permanently connected at the distal end to the rigid section of the outer tube 22, as is apparent from the illustration in FIG. 2.

The coupling 58 has an element 62 on whose outer side latching notches 66 in which a latch 68 engages are made.

The latch 68 is operatively connected to a knob 70, arranged on the housing 60, in such a way that activating the knob 70 causes the latch 68 to lift off from the latch notches 66. As a result, the coupling 58 is released, which also permits the outer tube 22 to rotate.

The handling and activation of the screwdriver 10 according to the invention will be explained briefly in the sequence from FIGS. 2 to 4.

In order to connect the outer tube 22 to the handle 14, the spring-loaded pin 36 is introduced into the groove 52 through the proximally open end of the groove 52.

An axial movement of the handle 14 causes the spring-loaded pin 36 which projects from the inner side of the handle 14 to be pushed in the distal direction along the groove 52 until it reaches the first locking point 28. The pin 36 engages in the depression 38 and is locked in the first locking point 28 as a result. A further axial advance displacement is not possible, since the groove 52 continues to the next axial section of the path 48 via a 90° step or bend. The distal flange of this step or bend provides the barrier for mechanically preventing a further axial movement of the handle 12.

The length of the outer tube 22 and that of the stem 16 are matched to one another in such a way that in the first locking position the screw 20 which is attached to the head 18 of the stem 16 is accommodated completely in the outer tube 22, as can also be seen in the illustration in FIG. 2.

In this first locking position 28, the screwdriver 10 according to the invention is introduced, with the screw 20 which is accommodated in the outer tube 22, into the operational area directly or via a trokar without the screw 20 being able to drop off the screwdriver 10.

In order to move the pin 36 from the first locking point 28 to the second locking point 30, the handle 14 must be rotated relative to the outer tube 21. This is forcibly guided by the guide 46 which is embodied as a groove 50, and the step blocks continuous linear displacement, without rotating.

At first, the handle 14 is rotated about the longitudinal axis 56, causing the pin 36 to be disengaged from the first locking point 28 guided along a first transverse section of the step. In order to guide the pin 36 along a second axial section of the step, the handle 14 is pushed forward axially after the pin has reached the end of the first section. The handle 14 is pushed forward until the pin 36 has moved to the level of the second locking point 30. The engagement of the spring-loaded pin 36 in the depression 40 causes the outer tube 22 to be locked in the second locking position with respect to the stem 16.

In this second locking position, the screw 20 protrudes partially in front of the outer tube 22 and as a result the screw 20 can be targeted at the destination at which it is to be screwed in.

As soon as the screw 20 has been aimed, the handle 14 is activated again.

The transfer of the pin 36 from the second locking point 30 to the third locking point 32 is again firstly carried out by rotation and subsequent axial movement of the handle 14.

In the third locking position 32, which can be seen in the illustration in FIG. 3, the screw 20 protrudes completely in front of the outer tube 22.

In this locking position 32, the screw 20, which is located at the destination can be screwed into the bone. The screwing in of the screw is brought about by rotating the handle 14 in the rightward direction. When the screw 20 is screwed in, one of the operator's hands grips the handle 14.

After the screw 20 has been screwed into the bone completely, the handle 14 is activated again in order to move the pin 36 from the third locking point 32 to the fourth locking point 34. This occurs again by a turning movement followed by an axial displacement.

In the fourth locking position 34, which is apparent from the illustration in FIG. 4 and into which the pin 36 is moved in the previously described way, the screw 20 is released from the distal end of the stem 16.

After the screw 20 has been released, the screwdriver 10 is removed from the patient's body.

The outer tube 22 and the handle 14 are separated from one another by guiding the pin 36 along the groove 54 as far as its open end. The screwdriver 10 can be thoroughly cleaned in a disassembled state.

Depending on how the coupling 58 is connected, the screw can be screwed into the right and the coupling runs freely to the left or the screw can be unscrewed to the left and the coupling is free running to the right.

Figure 5:
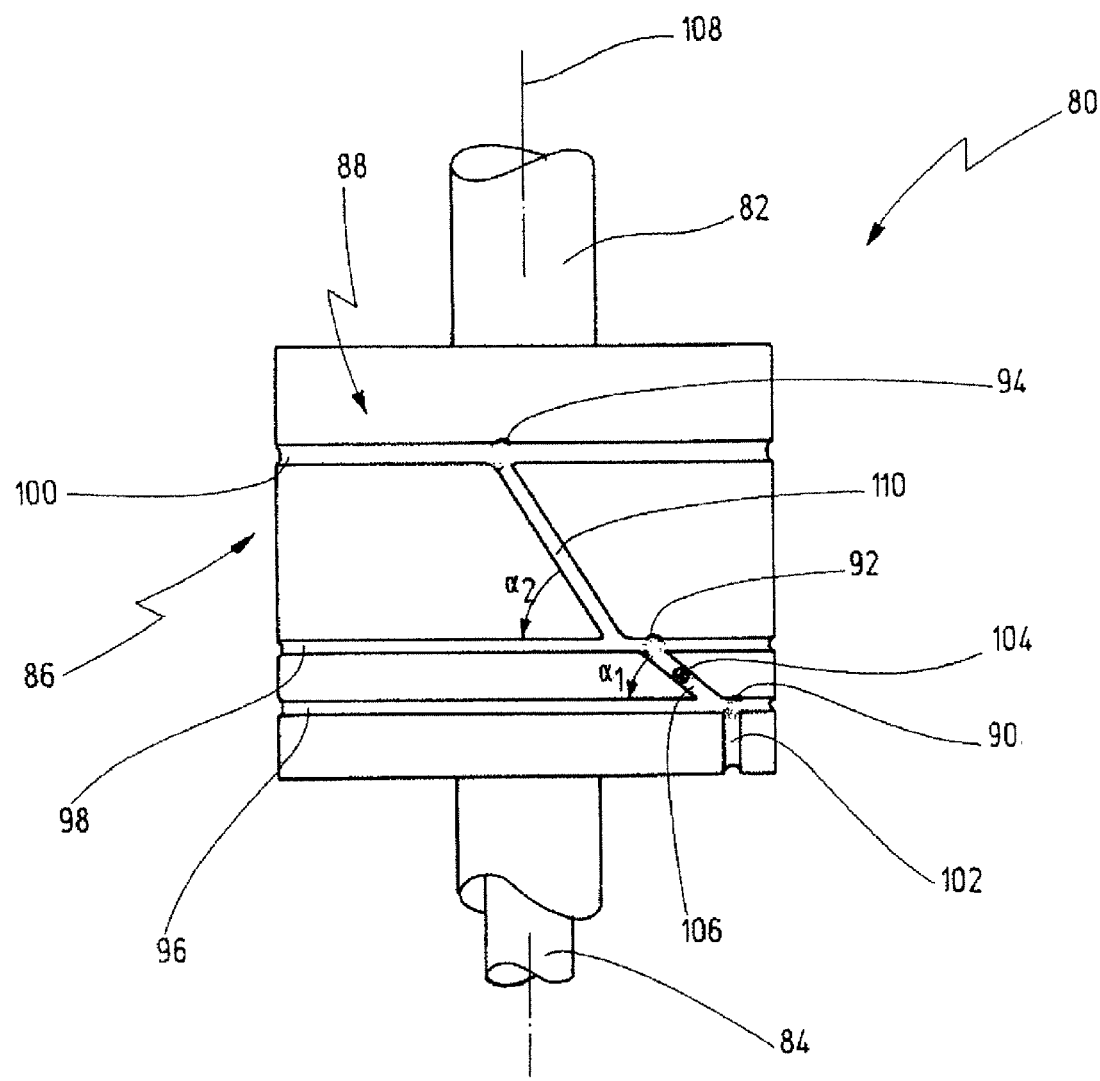
FIG. 5 shows a planar developed view of the guide in a further exemplary embodiment of a screwdriver.

FIG. 5 shows a further exemplary embodiment of part of a screwdriver 80. The outer tube 82 in which the stem 84 is inserted is illustrated.

FIG. 5 is a planar developed view 86 of part of the outer cylindrical circumferential face of the outer tube 82 in which the locking mechanism 88 is formed.

The locking mechanism 88 has three locking points 90, 92, 94 which are each provided in edges of circumferential annular grooves 96, 98 and 100 which are spaced apart from one another axially.

An insertion groove 102 extends in the axial direction, is open towards the proximal end and leads into the first locking point 90 in the circumferential groove 96.

The first circumferential annular groove 96 is connected to the next circumferential annular groove 98 via a path 104 which is inclined by the angle $\alpha_1$ about the longitudinal axis 108. The path 104 starts from the other side of the locking point 90.

This means that a locking element which projects from the inner side of the handle (not illustrated here) and is in the form of a pin 104 meets the locking point 90 in the first circumferential groove 96 after said locking element has firstly been inserted into the insertion groove 102. Further axial forward movement of the handle or of the pin 104 is not possible due to the mechanical barrier until the stem 84 or the handle and outer tube 82 which are connected to it have been rotated with respect to one another about the longitudinal axis 108. Only then can the pin 104 enter the inclined path 106 and be moved forward as far as the next locking point 92.

This corresponds to the previously described situation at which the tip of the screw protrudes somewhat out of the outer tube 82 so that it can be fitted onto the point which is to be screwed on.

In order to permit further axial forward movement of the pin, the stem 84 must be rotated again relative to the outer tube 82 about the longitudinal axis 108 so that the pin 104 can then enter the inclined path 110 and slide as far as the next locking point 94. This path 110 is also inclined by an angle $\alpha_2$ from the longitudinal axis 108.

In the illustrated exemplary embodiments, the angles $\alpha_1$ and $\alpha_2$ are different and they can be inclined to a greater or lesser extent but can also both be the same or be wound in the form of a helical line.

This design with the three circumferential annular grooves 96, 98, 100 which are spaced apart from one another corresponds to the prior art mentioned at the beginning, in which case according to the invention the measures are correspondingly taken according to which movement of the locking element from one groove to the other groove is made possible only by means of a relative rotational movement between the outer tube 82 and the stem 84.

What is claimed is:

1. A screwdriver for handling a screw in a body of a person or an animal, comprising:
    a handle,
    a stem permanently connected to said handle, said stem having a distal end to which a screw can be fitted,
    an outer tube surrounding said stem, and
    a locking mechanism for locking said outer tube in at least three different axial displacement positions relative to said stem, said locking mechanism having a locking element engaging into a locking point in each of said at least three different axial displacement positions of said outer tube, wherein
    said locking element is prevented from moving further in an axial direction at each locking point by a barrier, said barrier can be overcome only by rotating said outer tube and said stem relative to one another about a longitudinal axis, said locking element runs in a guide whose path deviates from a longitudinal axis by an angle $\alpha$ from one locking point to a next locking point, resulting in a stepped path, said stepped path having a locking point at a maximal advanced axial displacement position, and wherein said stepped path is connected to a return path extending from said maximal axial displacement position backwards to a level of a proximal end of said stepped path, and wherein said return path runs beside said stepped path.

2. The screwdriver of claim 1, wherein said angle $\alpha$ is about 30° to about 90°.

3. The screwdriver of claim 2, wherein said angle is approximately 90°.

4. The screwdriver of claim 1, wherein said path is embodied as a groove in said outer tube.

5. The screwdriver of claim 4, wherein said groove is embodied as a stepped groove.

6. The screwdriver of claim 1, wherein said locking element is embodied as a pin.

7. The screwdriver of claim 6, wherein said pin is a spring-loaded pin.

8. The screwdriver of claim 1, wherein said locking element projects from an inner side of said handle.

9. The screwdriver of claim 1, wherein said locking points are arranged at a proximal end section of said outer tube.

10. The screwdriver of claim 1, wherein a proximal end section of said outer tube can be rotated about a longitudinal axis.

11. The screwdriver of claim 10, wherein said rotatably proximal end section of said outer tube is connected to a coupling which runs freely to the right or to the left for rotating said outer tube.

12. The screwdriver of claim 1, wherein said outer tube is connected to said handle in a removable fashion.

13. The screwdriver of claim 1, wherein said locking points are embodied as depressions in said path.

14. The screwdriver of claim 1, wherein four locking points are provided.

15. The screwdriver of claim 1, wherein a groove which is open at its proximal end is formed from a proximal end of said outer tube up to a first locking point.

16. The screwdriver of claim 1, wherein a groove, which is open at its proximal end is formed from a last locking point to a proximal end of said outer tube.

* * * * *